United States Patent
Fujitani et al.

(10) Patent No.: US 7,945,396 B2
(45) Date of Patent: May 17, 2011

(54) MOLECULAR FORCE FIELD ASSIGNMENT METHOD, MOLECULAR FORCE FIELD ASSIGNMENT APPARATUS AND MOLECULAR FORCE FIELD ASSIGNMENT PROGRAM

(75) Inventors: Hideaki Fujitani, Kawaski (JP); Azuma Matsuura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 113 days.

(21) Appl. No.: 12/410,874

(22) Filed: Mar. 25, 2009

(65) Prior Publication Data

US 2009/0182514 A1    Jul. 16, 2009

Related U.S. Application Data

(63) Continuation of application No. PCT/JP2006/319593, filed on Sep. 29, 2006.

(51) Int. Cl.
*G01N 31/00* (2006.01)
(52) U.S. Cl. .............................. 702/27; 436/43
(58) Field of Classification Search .............. 702/27, 702/19, 182–185
See application file for complete search history.

(56) References Cited

U.S. PATENT DOCUMENTS

2008/0027652 A1* 1/2008 Cramer et al. ................ 702/19

FOREIGN PATENT DOCUMENTS

| JP | 60-215279 A | 10/1985 |
|----|----|----|
| JP | 2001-58962 A | 3/2001 |

OTHER PUBLICATIONS

S. Tebikisho; Chemterm/BLD; Fujitsu Ltd; Jul. 31, 1988; pp. 137-142, cited in ISR.
"Viewing the Shapes of Molecules by Computer," Shokabo Publishing Co., Ltd., Jan. 1, 2005; p. 31.
A. Jakalian et al. "Fast, Efficient Generation of High-Quality Atomic Charges. AM1-BCC Model: II. Parameterization and Validation," Journal of Computational Chemistry; vol. 23; Jan. 1, 2002; pp. 1623-1641.
J. Wang et al. "Antechamber, An Accessory Software Package for Molecular Mechanical Calculations," Submitted to Journal of Chemical Information and Computer Sciences; May 1, 2001; pp. 1-41.
International Search Report of PCT/JP2006/319593, date of mailing Oct. 31, 2006.

* cited by examiner

*Primary Examiner* — Edward Raymond
(74) *Attorney, Agent, or Firm* — Westerman, Hattori, Daniels & Adrian, LLP

(57) ABSTRACT

A molecular force field assignment method for assigning a molecular force field to a molecule having a desired molecular structure, includes a step of specifying a combination according to whether or not an interatomic distance between a first and second atoms, obtained by analyzing a molecular structure with a molecular orbital method, exceeds a prescribed threshold value.

9 Claims, 6 Drawing Sheets

MOLECULAR FORCE FIELD ASSIGNMENT METHOD, MOLECULAR FORCE FIELD ASSIGNMENT APPARATUS AND MOLECULAR FORCE FIELD ASSIGNMENT PROGRAM

CROSS-REFERENCE TO RELATED APPLICATIONS

This application is a continuation of international application PCT/JP2006/319593, filed on Sep. 29, 2006.

TECHNICAL FIELD

The present invention relates to a method for specifying a combination of an atom type and a bond type of an atomic pair constituting a molecule having a desired molecular structure in order to assign a molecular force field to that molecule, and more particularly, to a method for specifying a combination of an atom type and a bond type by comparing an interatomic distance calculated with the molecular orbital method with a prescribed threshold value.

BACKGROUND ART

A molecular force field refers to a field of force acting on each atom that comprises a molecule. Thus, if a molecular force field is known, the geometrical structure, electronic properties, physical properties and reactivity of a molecule can be simulated. For example, a simulation can be carried out to determine the manner in which a candidate substance of a new drug reacts with a known protein comprising the human body or a virus.

This type of simulation is referred to as a molecular orbital method calculation in the case the force field used in the calculation is represented by a function based on quantum mechanics. On the other hand, this type of simulation is referred to as a molecular mechanics calculation or molecular force field method in the case the force field used in the calculation is represented by a function based on classical physics.

In a molecular orbital method calculation, the molecular orbital function is determined by solving a Schrödinger equation. Thus, a highly precise solution is obtained that takes into consideration quantum effects. However, the calculation becomes difficult as the number of atoms that compose the molecule increases since the number of calculations rapidly increases.

Consequently, molecular force field calculations were created to simulate the structures of molecules having a large number of constituent atoms in the manner of organic compounds. The functions used in molecular force field calculations are classical potential functions, primary examples of which include bond stretching energy obtained by hypothesizing that elastic force in the manner of a spring acts between atoms, angle bending energy of a bond angle similarly based on the hypothesis that elastic force acts between bonds of the same atom, torsion energy based on the hypothesis that elastic force acts between dihedral angles, van der Walls non-bonding interaction energy, and electrostatic interaction energy between ions ("Viewing the Shapes of Molecules by Computer", Shokabo Publishing Co., Ltd., 2005, p. 31.).

An example of a simulation in which the molecule force field calculation demonstrates its effectiveness is conformational analysis. Even though an organic compound may have the same molecular formula, it may have a plurality of possible three-dimensional structures. In such cases, use of a molecular force field calculation makes it possible to determine which of the structures are stable (conformational analysis).

On the other hand, molecular dynamics calculations, which analyze interactions between molecules in accordance with Newton's equation of motion by hypothesizing that forces of classical dynamics act between molecules, are effective in predicting reactivity between molecules as well as the equilibrium state and physical properties of molecule groups. Since molecule dynamics calculations analyze molecular interactions and the passage of time, the number of calculations is far greater than that of molecular mechanics calculations. Thus, classical potential functions, for which calculations are easier, are used as functions for representing molecular force fields in the same manner as the molecular force field method. However, the objects of molecular dynamics calculations are molecule groups in which interactions acting between molecules are comprised only of non-bonding interactions. Namely, molecular dynamics calculations only take into consideration electrostatic interaction energy and van der Waals non-bonding interaction energy.

Molecular orbital method calculations have been able to be applied even to considerably large molecules due to the significant improvement in the processing speeds of computers. Thus, the number of molecular structure calculations forced to rely on molecular force field calculations is decreasing. However, even if using current high-speed computers, it is still difficult to analyze molecular interactions and passage of time by quantum mechanics. Thus, molecular dynamics calculations have not declined in importance even at present.

On the contrary, molecular simulations using molecular dynamics calculations are actively used in the fields of biochemistry by utilizing high-speed computers. In order to develop a new drug, it is necessary to comprehensively produce new drug candidate substances and then test reactions between the drug and proteins it is to act on (consisting mainly of reactions resulting from clone interactions between atoms forming molecules). However, if it were possible to predict the reaction between a new drug candidate substance and a target protein by molecular dynamics calculations, it would be possible to considerably reduce development costs and shorten development time. Thus, molecular dynamics calculations are extremely important in the development of new drugs.

Furthermore, in the case of talking about molecular force fields, this usually refers to the classical potential used in molecular force field calculations or molecular dynamics calculations. Thus, a molecular force field (or force field) hereinafter refers to the classical potential used in molecular force field calculations or molecular dynamics calculations.

Non-Patent Document 1: "Viewing the Shapes of Molecules by Computer", Shokabo Publishing Co., Ltd., 2005, p. 31.

Non-Patent Document 2: "Fast, Efficient Generation of High-Quality Atomic Charge, AM1-BCC Model II, Parameterization and Validation", Journal of Computational Chemistry, Vol. 23, p. 1623-1641, 2002.

DISCLOSURE OF INVENTION

Problems to be Solved by the Invention

Highly precise programs for molecule force field calculations and molecule dynamics calculations have already been developed. Typical examples of such programs include AMBER for biochemistry, MM3 and MM4 for organic chemistry, and CHARM, which can be applied to various types of substances. In these programs, molecular force fields are provided that match the respective objective. For example, in the case of MM3 and MM4, in addition to molecular force fields such as stretching energy, angle bending energy and torsion energy, correction terms such as out-of-plane angle bending energy, stretching-angle bending energy and angle bending-angle bending energy are also taken into consideration in order to precisely analyze organic substances. Moreover, stretching energy, angle bending energy and torsion energy use complex and precise functions ("Viewing the Shapes of Molecules by Computer", Shokabo Publishing Co., Ltd., 2005, p. 31).

The availability of such software facilitates the carrying out of molecular force field calculations and molecule dynamics calculations. However, in the case of attempting to simulate a novel compound, which molecular force fields may be assigned to the atoms that compose that compound or the bonds between atoms becomes a problem. If this assignment is not correct, results are obtained that are quite different from the actual compound in question. The following provides an explanation of processing performed with AMBER used to resolve this problem.

It is known that if it were possible to specify atom type and bond type, then a molecular force field to be assigned to an atom (and bond between atoms) could be specified based on that information. Bond type refers to the type of bond, and in the case of carbon, for example, includes single bonds equivalent to the $sp^3$ hybrid orbital, double bonds equivalent to the $sp^2$ hybrid orbital, triple bonds equivalent to the sp hybrid orbital, aromatic single bonds and aromatic double bonds. On the other hand, atom type refers to the classification of similar atoms according to "differences in bonding state". For example, nitrogen atoms are classified into amine nitrogen, divalent anionic nitrogen, trivalent nitrogen, neutral divalent nitrogen, univalent nitrogen, cationic divalent nitrogen and the like ("Fast, Efficient Generation of High-Quality Atomic Charge, AM1-BCC Model II, Parameterization and Validation", Journal of Computational Chemistry, Vol. 23, p. 1623-1641, 2002).

The conceiving of a novel compound is none other than conceiving a molecular structure, namely the constituent atoms and the manner in which the constituent atoms are bonded to other constituent atoms. In other words, the first stage includes determining the types of atoms (elements) that compose the compound and the manner in which those atoms are bound to each other. There are many cases in which the atom type and bond type of each atom are determined automatically based on the molecular structure. However, there are also cases in which they are not so easily determined.

For example, assume that a compound has been conceived represented by the chemical formula $C_2H_5N_2$ and having a structure like that depicted as FIG. 4. In this drawing, the atom types and bond types between atoms are not specified. Thus, the bonds between atoms are indicated with broken lines. There can be readily seen to be only two possible ways of assigning the atom types and bond types based on the molecular structure of FIG. 4 as depicted as FIG. 5A and FIG. 5B. If the atom type and bond type assigned to the pair of nitrogen atoms depicted on the left end of the molecule are excluded, there is only one possible way of assigning the atom types and bond types. Thus, a molecular force field can immediately be assigned to the atoms and bonds excluding the pair of nitrogen atoms and their bonds.

However, a molecular force field can still not be assigned to the pair of nitrogen atoms on the left end.

The following provides an explanation of the manner in which a molecular force field is assigned to the pair of atoms on the left end with respect to the above-mentioned compound $C_2H_5N_2$.

First, for the sake of explanation, a brief explanation is provided of the structures of FIG. 5A and FIG. 5B. In FIG. 5A, a first nitrogen atom 1 is electrically neutral and has a valence of 3. In FIG. 5B, a first nitrogen atom 1 is ionized to an anion and has a valence of 2. In addition, in FIG. 5A, a second nitrogen atom 3 is ionized to a cation and has a valence of 4. In FIG. 5B, a second nitrogen atom 3 is electrically neutral and has a valence of 3. On the other hand, a bond 2 between the nitrogen atoms is a triple bond in FIG. 5A and a double bond in FIG. 5B.

The bond type between such nitrogen atoms is classified as a triple bond for the bond of FIG. 5A and a double bond for the bond of FIG. 5B. On the other hand, with respect to atom type, the first nitrogen atom of FIG. 5A is classified as a univalent nitrogen, while the second nitrogen atom of FIG. 5A is classified as a cationic divalent nitrogen. The first nitrogen atom of FIG. 5B is classified as a univalent nitrogen, while the second nitrogen atom of FIG. 5B is classified as a neutral divalent nitrogen.

In the AMBER program, bond types and atom types are further encoded. Different bond types and different atom types are given different codes as a general rule. However, there are also cases in which the same code is given. This is done to improve the efficiency of molecular force field assignment processing by assigning the same code in the case there are no differences in the ultimately assigned molecular force fields ("Fast, Efficient Generation of High-Quality Atomic Charge, AM1-BCC Model II, Parameterization and Validation", Journal of Computational Chemistry, Vol. 23, p. 1623-1641, 2002).

In the AMBER program, combinations of atom types and bond types are specified for various atomic pairs using these codes. For example, the pair of nitrogen atoms of FIG. 5A is accommodated with 25-03-25 by combining a code 25 for the univalent nitrogen, a code 03 for the triple bond and a code 25 for the cationic divalent nitrogen. On the other hand, the pair of nitrogen atoms of FIG. 5B are accommodated with 25-02-24 by combining a code 25 for the univalent nitrogen, a code 02 for the double bond, and a code 24 for the neutral divalent nitrogen.

The AMBER program records molecular force field functions to be assigned to each atomic pair for such combinations of codes in a database. Thus, if the "combination of atom type and bond type" for the pair of nitrogen atoms of FIG. 4 is specified as 25-03-25, for example, the molecular force field corresponding to 25-03-25 is read from the database and assigned to the pair of nitrogen atoms (two nitrogens and an inter-nitrogen bond). Which code among either 25-03-24 or 25-03-25 may be assigned to the pair of nitrogen atoms is determined in the manner described below.

As previously described, there are cases in which a "combination of atom type and bond type" to be assigned to an atomic pair present in a certain molecule is not able to be specified to a single combination even if using knowledge relating to chemical bonds. However, in the case such an atomic pair belongs to a fragment of a certain size (group of atoms forming the molecule), it is empirically known that there is only one "combination of atom type and bond type" of that atomic pair belonging to that fragment. The AMBER program utilizes this fact to preliminarily record the above fragment and "combination of atom type and bond type" of atomic pair belonging thereto in a database.

When specifying a "combination of atom type and bond type" for a certain atomic pair, a fragment containing that atomic pair is first read from the above-mentioned database followed by confirming whether that fragment is present in the molecule for which a force field is attempting to be assigned. If the read fragment is not present in this molecule, a different fragment is read from the database. Once a read fragment is found in the molecule by repeating this procedure, that fragment along with the "combination of atom type and bond type" recorded in the database are assigned to the above-mentioned atomic pair.

For example, the procedure for assigning a "combination of atom type and bond type" to the pair of nitrogen atoms present on the left side of the molecule depicted as FIG. 4 is described below. An $N_2C_2H_2$— fragment as depicted as FIG. 6 and the atom type/bond type code combination of 25-03-25 for the pair of nitrogen atoms in this fragment are recorded in the database.

The AMBER program sequentially reads out fragments containing pairs of nitrogen atoms from the database. In the case a fragment other than an $N_2C_2H_2$— fragment (including nitrogen atoms) has been read, since that fragment is not present in the molecule of FIG. 4, a different fragment is read and that fragment is investigated again as to whether it is present in the molecule. As the program repeats this testing, it eventually reaches the $N_2C_2H_2$— fragment. Since the $N_2C_2H_2$— fragment is definitely present in the molecule of FIG. 4, the atom type/bond type code combination of 25-03-25 recorded in the database is assigned to the pair of nitrogen atoms of FIG. 4.

In this manner, the atom type/bond type combination code 25-03-25 is assigned to the nitrogen pair of FIG. 4.

However, a "combination of atom type and bond type" recorded in the database is experimentally specified for each individual fragment after having investigated various properties of molecules that actually exist. Moreover, in order to specify a single "combination of atom type and bond type", the fragment serving as the base material have a certain size as depicted as FIG. 6, for example. For example, the fragment depicted as FIG. 6 also contains atoms present at two remote locations from the pair of nitrogen atoms.

Thus, in the case of attempting to assign a molecular force field to a novel compound, there are frequently cases in which a fragment containing an atomic pair in the compound is not present in the database or even if such a fragment is present, there are cases in which the fragment is not present in the compound.

Therefore, an object of the present invention is to provide a molecular force field assignment method, a molecular force field assignment apparatus and a molecule force field assignment program capable of assigning suitable molecular force fields even for novel compounds.

Solution to Problem

To achieve the above-described objects, a first aspect of the present invention is characterized in that a molecular force field assignment method for assigning a molecular force field to a molecule having a desired molecular structure, includes: a first step of, in a case a single combination is unable to be specified from candidates for a combination made up of respective atom types of mutually bonded first and second atoms constituting the molecule and a bond type of a bond connecting the first and second atoms, specifying candidates for the combination that satisfy both first fragment information indicative of a type of an atom bound to the first atom, a coordination number of the first atom, and a valence able to be adopted by the first atom, and second fragment information indicative of a type of an atom bound to the second atom, a coordination number of the second atom, and a valence able to be adopted by the second atom; a second step of specifying the combination from among the candidates specified in the first step according to whether or not an interatomic distance between the first and second atoms, obtained by analyzing the molecular structure with a molecular orbital method, exceeds a prescribed threshold value; and a third step of assigning a molecular force field to the first and second atoms and the bond, based on the combination specified in the second step.

According to a first aspect thereof, the present invention is able to provide a molecular force field assignment method capable of assigning suitable molecular force fields even for novel compounds.

A second aspect of the present invention, in the first aspect, is characterized in that the prescribed threshold value is determined based on the interatomic distance obtained by analyzing a molecular structure of a molecule, having the first and second atoms for which the combination thereof has been specified, with a molecular orbital method.

A third aspect of the present invention, in the first or second aspect, is characterized in that, in a case the desired molecular structure is a structure in which the first and second atoms are nitrogen atoms, the first atom is bound only to the second atom, and the second atom is bound only to a carbon atom, the second step includes: specifying, as the combination, a candidate in which atom types of the first and second atoms are a neutral univalent nitrogen and a cationic divalent nitrogen, respectively, and a bond type of a bond connecting the first and second atoms is a triple bond in a case the interatomic distance between the first and second atoms as obtained by analyzing the molecular structure with a molecular orbital method is less than 0.112 nm, specifying, as the combination, a candidate in which atom types of the first and second atoms are an anionic univalent nitrogen and a cationic divalent nitrogen, respectively, and a bond type of a bond connecting the first and second atoms is a double bond in a case the interatomic distance between the first and second atoms as obtained by analyzing the molecular structure with a molecular orbital method is more than 0.112 nm but less than 0.115 nm, and specifying, as the combination, a candidate in which atom types of the first and second atoms are an anionic univalent nitrogen and a neutral divalent nitrogen, respectively, and a bond type of a bond connecting the first and second atoms is a double bond in a case the interatomic distance between the first and second atoms as obtained by analyzing the molecular structure with a molecular orbital method is more than 0.115 nm.

According to a third aspect thereof, the present invention is able to provide a molecular force field assignment method capable of assigning suitable molecular force fields to nitrogen atom pairs bonded to carbon atoms even for novel compounds.

A fourth aspect of the present invention is characterized in that a molecular force field assignment apparatus for assigning a molecular force field to a molecule having a desired molecular structure, includes: a first unit which, in a case a single combination is unable to be specified from candidates for combination made up of respective atom types of mutually bonded first and second atoms constituting the molecule and a bond type of a bond connecting the first and second atoms, specifies candidates for the combination that satisfy both first fragment information indicative of a type of an atom bound to the first atom, a coordination number of the first atom, and a valence able to be adopted by the first atom, and second fragment information indicative of a type of an atom bound to the second atom, a coordination number of the second atom, and a valence able to be adopted by the second atom; a second unit which specifies the combination from among the candidates specified by the first unit according to whether or not an interatomic distance between the first and second atoms, obtained by analyzing the molecular structure with a molecular orbital method, exceeds a prescribed threshold value; and a third unit which assigns a molecular force field to the first and second atoms and the bond, based on the combination specified by the second unit.

According to a fourth aspect thereof, the present invention is able to provide a molecular force field assignment apparatus capable of assigning suitable molecular force fields even for novel compounds. A fifth aspect of the present invention, in the fourth aspect, is characterized in that the prescribed threshold value is determined based on the interatomic distance obtained by analyzing a molecular structure of a molecule, having the first and second atoms for which the combination thereof has been specified, with a molecular orbital method.

A sixth aspect of the present invention, in the fourth or fifth aspect, is characterized in that, The molecular force field assignment apparatus according to claim 4 or 5, wherein, in a case the desired molecular structure is a structure in which the first and second atoms are nitrogen atoms, the first atom is bound only to the second atom, and the second atom is bound only to a carbon atom, the second unit: specifies, as the combination, a candidate in which atom types of the first and second atoms are a neutral univalent nitrogen and a cationic divalent nitrogen, respectively, and a bond type of a bond connecting the first and second atoms is a triple bond in a case the interatomic distance between the first and second atoms as obtained by analyzing the molecular structure with a molecular orbital method is less than 0.112 nm, specifies, as the combination, a candidate in which atom types of the first and second atoms are an anionic univalent nitrogen and a cationic divalent nitrogen, respectively, and a bond type of a bond connecting the first and second atoms is a double bond in a case the interatomic distance between the first and second atoms as obtained by analyzing the molecular structure with a molecular orbital method is more than 0.112 nm but less than 0.115 nm, and specifies, as the combination, a candidate in which atom types of the first and second atoms are an anionic univalent nitrogen and a neutral divalent nitrogen, respectively, and a bond type of a bond connecting the first and second atoms is a double bond in a case the interatomic distance between the first and second atoms as obtained by analyzing the molecular structure with a molecular orbital method is more than 0.115 nm.

According to a sixth aspect thereof, the present invention is able to provide a molecular force field assignment apparatus capable of assigning suitable molecular force fields to nitrogen atom pairs bonded to carbon atoms even for novel compounds.

A seventh aspect of the present invention is characterized in that a molecular force field assignment program for causing a computer to carry out molecular force field assignment processing for assigning a molecular force field to a molecule having a desired molecular structure, the program causing the computer to execute: a first step of, in a case a single combination is unable to be specified from candidates for a combinations made up of respective atom types of mutually bonded first and second atoms constituting the molecule and a bond type of a bond connecting the first and second atoms, specifying candidates for the combination that satisfy both first fragment information indicative of a type of an atom bound to the first atom, a coordination number of the first atom, and a valence able to be adopted by the first atom, and second fragment information indicative of a type of an atom bound to the second atom, a coordination number of the second atom, and the valence able to be adopted by the second atom; a second step of specifying the combination from among the candidates specified in the first step according to whether or not an interatomic distance between the first and second atoms, obtained by analyzing the molecular structure with a molecular orbital method, exceeds a prescribed threshold value; and a third step of assigning a molecular force field to the first and second atoms and the bond, based on the combination specified in the second step.

According to a seventh aspect thereof, the present invention is able to provide a molecular force field assignment program capable of assigning suitable magnetic force fields even for novel compounds.

An eighth aspect of the present invention, in the seventh aspect, is characterized in that the prescribed threshold value is determined based on the interatomic distance obtained by analyzing a molecular structure of a molecule, having the first and second atoms for which the combination thereof has been specified, with a molecular orbital method.

A ninth aspect of the present invention, in the eighth or seventh aspect, is characterized in that, in a case the desired molecular structure is a structure in which the first and second atoms are nitrogen atoms, the first atom is bound only to the second atom, and the second atom is bound only to a carbon atom, the second step includes: specifying, as the combination, a candidate in which atom types of the first and second atoms are a neutral univalent nitrogen and a cationic divalent nitrogen, respectively, and a bond type of a bond connecting the first and second atoms is a triple bond in a case the interatomic distance between the first and second atoms as obtained by analyzing the molecular structure with a molecular orbital method is less than 0.112 nm, specifying, as the combination, a candidate in which atom types of the first and second atoms are an anionic univalent nitrogen and a cationic divalent nitrogen, respectively, and a bond type of a bond connecting the first and second atoms is a double bond in a case the interatomic distance between the first and second atoms as obtained by analyzing the molecular structure with a molecular orbital method is more than 0.112 nm but less than 0.115 nm, and specifying, as the combination, a candidate in which atom types of the first and second atoms are an anionic univalent nitrogen and a neutral divalent nitrogen, respectively, and a bond type of a bond connecting the first and second atoms is a double bond in a case the interatomic distance between the first and second atoms as obtained by analyzing the molecular structure with a molecular orbital method is more than 0.115 nm.

According to a ninth aspect thereof, the present invention is able to provide a molecular force field assignment program capable of assigning suitable molecular force fields to nitrogen atom pairs bonded to carbon atoms even for novel compounds.

Effect of the Invention

According to the present invention, suitable molecular force fields can be assigned even for novel compounds.

BEST MODE FOR CARRYING OUT INVENTION

The following provides an explanation of embodiments of the present invention according to drawings. The protective scope of the present invention covers the inventions defined in the claims and their equivalents, but is not limited to the above embodiments.

(1) Principle

As has been previously described, conventional molecular force field calculation programs (or molecular dynamics calculation programs) experimentally determine the fragments that form an existing molecule and "combinations of atom type and bond type" of atomic pairs contained therein, and then specify a "combination of atom type and bond type" of an atomic pair present in the molecular targeted for calculation based on that information.

In contrast, the inventor of the present invention focused on being able to automatically specify an atom type by specifying a bond type between an atomic pair provided that candidates of a "combination of atom type and bond type" can be narrowed down to a certain range. For example, in the compound of FIG. 4, if the bond type between nitrogens is specified to be a triple bond, the "combination of atom type and bond type" of the nitrogen pair is readily specified to be the combination depicted as FIG. 5A. However, if the bond type between an atomic pair is attempted to be specified, there was no choice in the prior art but to actually synthesize that substance and then specify the bond type experimentally. If this is the case, then the significance of molecular simulation of novel compounds ends up being lost.

On the other hand, the structure of a compound can be analyzed using the molecular orbital method even if the compound is unknown. However, results obtained with the molecular orbital method are an electron density function, and it is difficult to specify bond types from this electron density function. However, the inventor of the present invention conducted an extensive study to determine the existence of a parameter connecting analytical results to experimentally identified bond types by analyzing the structures of a large number of presently known molecules using the molecular orbital method. As a result, interatomic distance (distance between atomic nuclei) calculated with the molecular orbital method was found to demonstrate a strong correlation with experimentally identified bond types.

Figure 7:
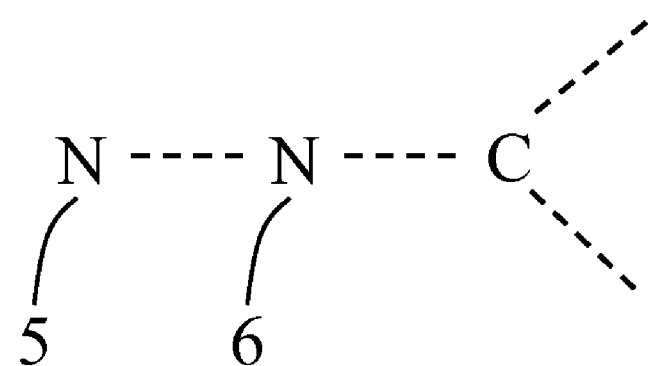
FIG. 7 is an example of small fragment.

For example, assume that the atomic configuration having the lowest total molecular energy is specified by analyzing molecules containing fragments which include N—N—C as depicted as FIG. 7 using the molecular orbital method. The distance between nitrogen atoms 5 and 6 can be easily calculated from the resulting atomic configuration. If the calculated nitrogen interatomic distance is shorter than 0.112 nm, the experimentally determined bond type between the nitrogen atoms is always a triple bond. On the other hand, in the case the calculated nitrogen interatomic distance is longer than 0.112 nm but shorter than 0.115 nm, the bond type between the nitrogen atoms is always a anionic-cationic double bond. Moreover, in the case the calculated nitrogen interatomic distance is longer than 0.115 nm, the bond type between the nitrogen atoms is always an anionic-neutral atom double bond. Values for specifying bond type in the manner of the values of 0.112 nm or 0.115 nm as indicated above will hereinafter be referred to as threshold values.

The coordination number (number of other atoms bound by that atom) of the carbon C depicted as FIG. 7 is 3. However, the above-mentioned threshold value is valid even in cases of a coordinate number for carbon C of 2 or 4.

Thus, a "combination of atom type and bond type" can be specified by calculating the interatomic distance in a stable state with the molecular orbital method and then comparing that value with a threshold value.

The above-mentioned threshold value is not determined for each atomic pair, but rather is determined for each fragment. For example, in the example depicted as FIG. 7, the threshold values of 0.112 nm and 0.115 nm are not specified for the nitrogen atomic pair N—N, but rather are specified for the fragment N—N—C.

However, this fragment is small in scale, consisting only of the addition of a single carbon atom to a pair of nitrogen atoms. If the scale of a fragment is small in this manner, nearly all possible fragments can be found among existing compounds. Thus, threshold values can be specified for nearly all fragments based on a comparison of data relating to existing bond types and interatomic distances determined with the molecular orbital method.

Thus, according to the present invention, a threshold value as described above can be found even for atomic pairs in novel compounds. Thus, molecular force fields can be assigned even for atomic pairs in novel compounds. Furthermore, fragments correlated with threshold values in the above manner will hereinafter be referred to as subfragments.

On the other hand, in the AMBER program, a "combination of atom type and bond type" is specified for a known fragment and an atomic pair within that fragment. Thus, if that fragment is fortunate enough to be present in the molecule to be analyzed, a molecule force field can be assigned. However, the fragment is required to be of a certain size. Thus, even if a molecular force field is attempted to be assigned to a novel compound, there are cases in which a fragment matching a fragment recorded in a database may not be present in the compound for which a molecular force field is to be assigned. In such cases, a molecular force field is unable to be assigned and a molecular force field calculation (or molecular dynamics calculation) is not able to be applied.

(2) Apparatus Configuration

Figure 1:
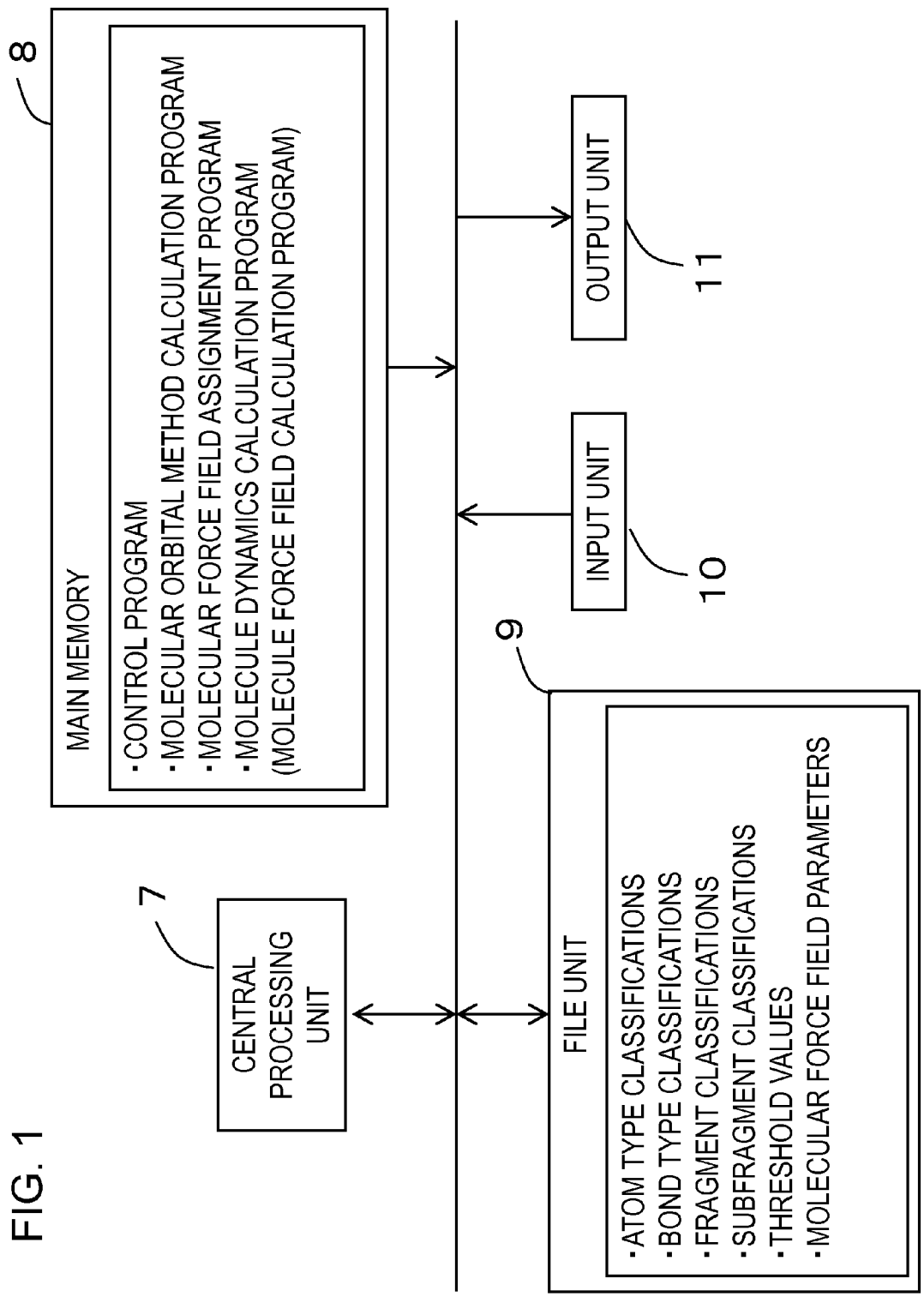
FIG. 1 is a schematic drawing of an analytical apparatus used to carry out the present invention.

FIG. 1 is a schematic drawing of an analytical apparatus used to carry out the present invention. This apparatus not only assign molecular force fields, but also perform molecule dynamics calculations (or molecular force field calculations).

This apparatus is provided with a central processing unit 7 for arithmetic processing, a main memory 8, a file unit 9, an input unit 10 and an output unit 11.

A control program, a molecular orbital method calculation program, a molecular force field assignment program for assigning molecular force fields, and a molecular dynamics calculation program (or molecular force field calculation program) for molecular dynamics calculations (or molecular force field calculations) are recorded in the main memory 8.

On the other hand, atom type classifications, bond type classifications, fragment classifications, subfragment classifications, threshold values and molecular force field parameters (parameters used with a molecular force field function), which are used in the molecular force field assignment program, are recorded in the file unit 9.

(3) Calculation Procedure

Figure 2:
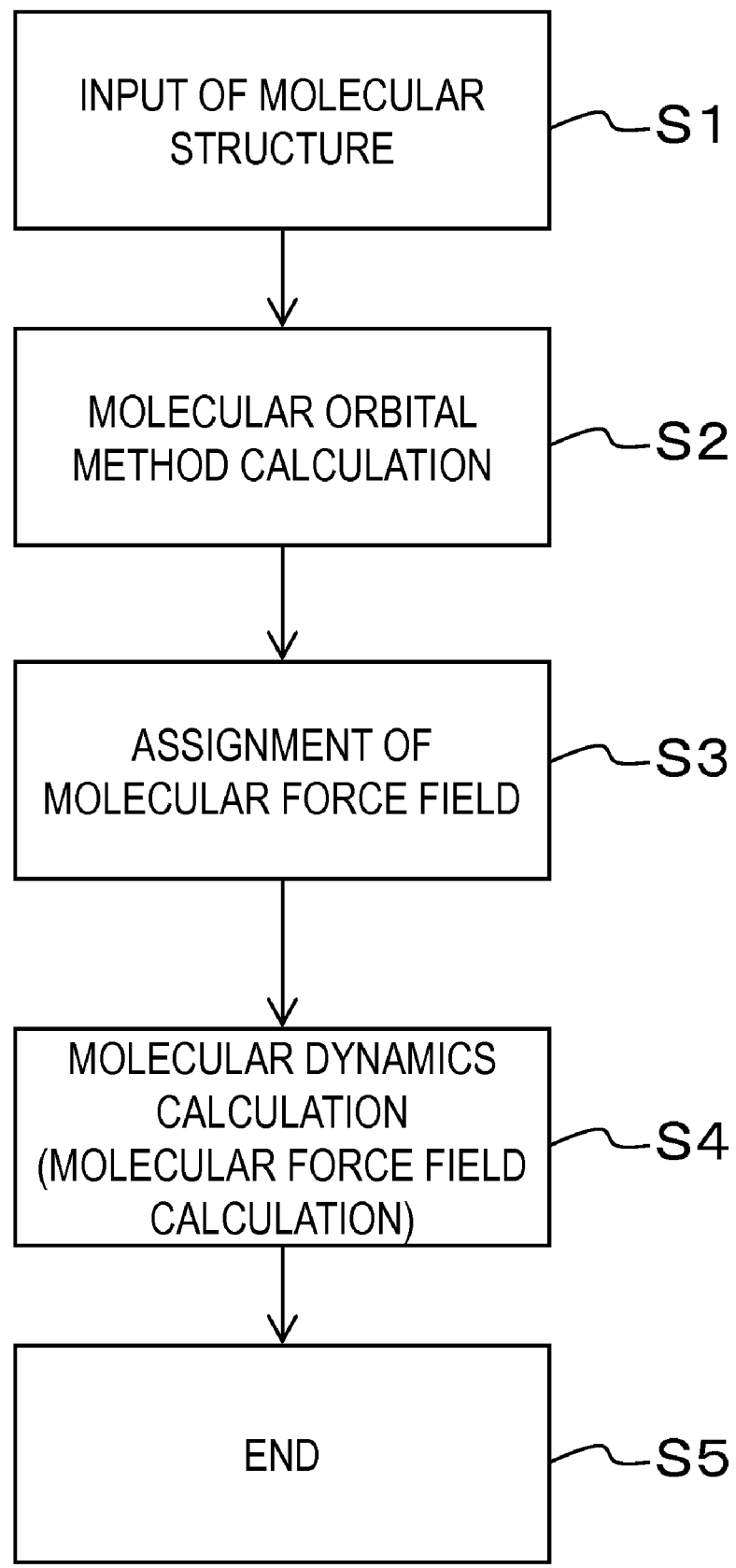
FIG. 2 is a flowchart of first processing executed by the analytical apparatus according to the embodiment.
Figure 3:
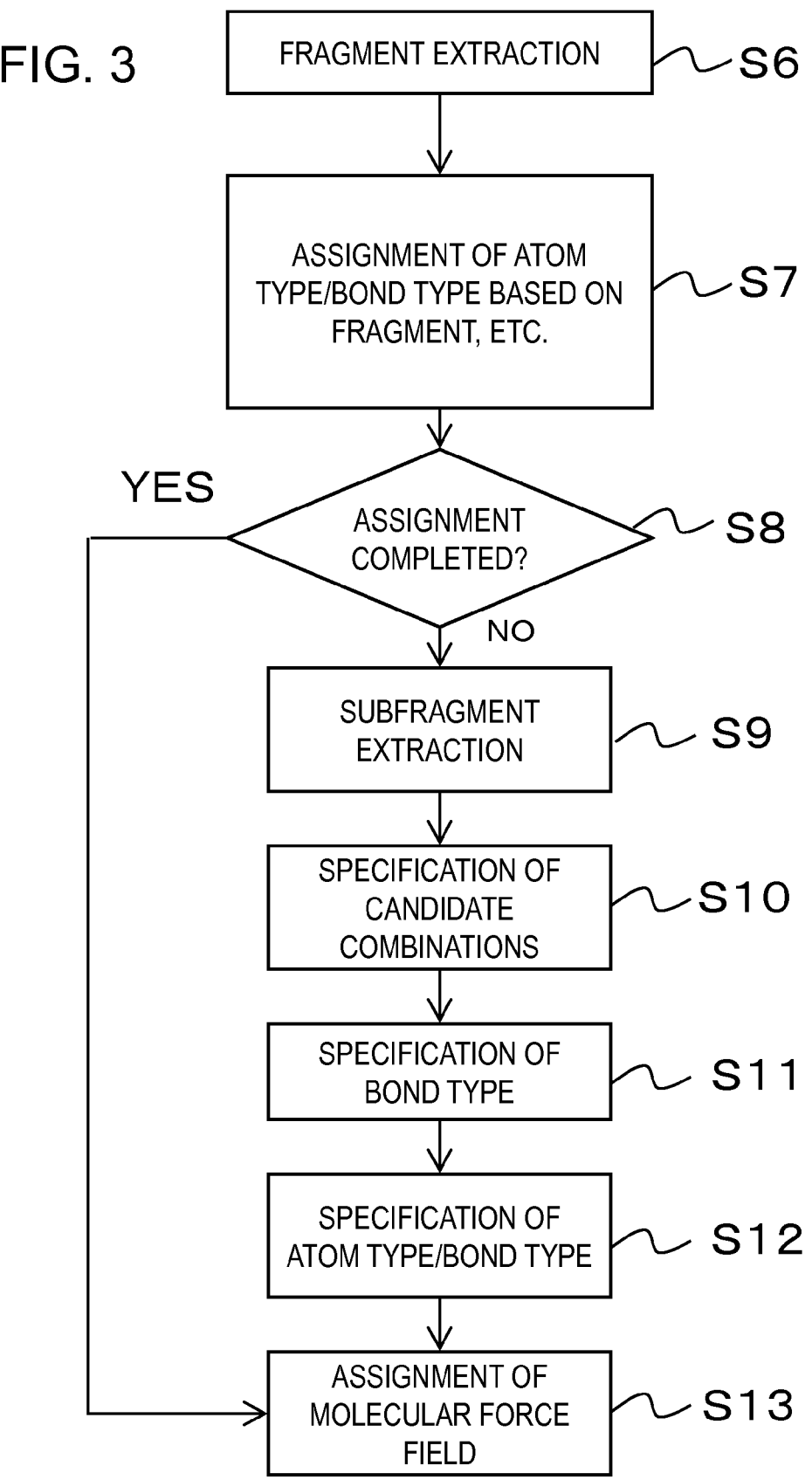
FIG. 3 is a flowchart of second processing executed by the analytical apparatus according to the embodiment.

FIG. 2 and FIG. 3 are flowcharts of processing executed by the apparatus depicted as FIG. 1. FIG. 2 depicts the overall processing flow, while FIG. 3 depicts details of molecular force field assignment processing.

First, the molecular structure of a molecule to be analyzed is input from the input unit 10 (S1). Input data include information as to the type of atom (element) and which atoms are bonded to which atom as depicted as FIG. 4, for example.

The central processing unit 7 then receives a command from the control program in the main memory 8, accesses the molecular orbital method calculation program, carries out a molecular orbital method calculation on the input molecular structure, and calculates the orbital function and atomic configuration having the lowest total molecular energy for the input molecular structure (S2).

Next, the central processing unit 7 receives a command from the control program in the main memory 8, accesses the molecular force field assignment program, and assigns a molecular force field based on the results of the previous processing (S2) and the input molecular structure. This processing uses each of the files recorded in the file unit 9 (S3).

Moreover, the central processing unit 7 receives a command from the control program in the main memory 8, accesses the molecular dynamics calculation program (or molecule force field calculation program), performs a molecular dynamics calculation (or molecule force field calculation program) based on the processing result of the molecular force field assignment program and the input molecular structure, and outputs that result to the output unit 11 (S4).

This completes the processing of the apparatus depicted as FIG. 1 (S5).

FIG. 3 depicts the details of the molecular force field assignment processing (S3) described above.

First, the central processing unit 7 receives a command from the molecular force field assignment program, accesses fragment classifications from the file unit 9, and extracts corresponding fragments from the input molecular structure. The extracted fragments are those for which the atom types of atoms and bond types of bonds belonging to the fragments are known, examples of which include nitro groups, phosphate groups, sulfone groups, amides, lactans and lactones (S6).

Next, the central processing unit 7 receives a command from the molecule force field assignment program, and assigns atom types and bond types determined on the basis of experimental results to atoms and bonds in the above-mentioned fragment (S7). Furthermore, the identities of the assigned atom types and bond types are recorded in the file unit 9 together with the above-mentioned fragment classifications.

In the case processing for assigning "atom type and bond type" to all of the atoms and bonds in the input molecular structure has been completed as a result of the assignment processing described above (S8), the central processing unit 7 receives a command from the molecular force field assignment program, and assigns a molecular force field to the input molecular structure based on the assigned atom types and bond types (S13). The central processing unit 7 accesses force field parameters from the file unit 9 and assigns these parameters to each atom or bond in order to perform molecular force field assignment processing.

In the case assignment of "atom types and bonds types" is not completed (S8), the central processing unit 7 receives a command from the molecular force field assignment program, and extracts a subfragment that contains an atomic pair unable to be assigned and matches the input molecular structure from the subfragment classifications in the file unit 8 (S9).

Next, the central processing unit 7 receives a command from the molecular force field assignment program, and specifies candidate combinations of "atom type and bond type" for the above-mentioned atomic pair based on the input molecular structure (S10). Specification of the candidate combinations is executed based on fragment information including the types of atoms (elements) bound to each atom that forms the atomic pair, the coordination number of each atom, and the valence able to be adopted by each atom.

Next, the central processing unit 7 receives a command from the molecular force field assignment program, accesses a threshold value correlating to the extracted subfragment from the file unit 8, and compares that threshold value with an interatomic distance calculated with the molecular orbital method to specify the bond type of the bond between the above-mentioned atomic pair (S11).

Next, the central processing unit 7 receives a command from the molecular force field assignment program, and specifies a "combination of atom type and bond type" for the atomic pair based on the specified bond type and candidate combinations (S12).

Finally, the central processing unit 7 receives a command from the molecular force field assignment program, and assigns a molecular force field to the input molecular structure (S13) based on the assigned "atom type and bond type" (S7) and the specified "atom type and bond type" (S12).

Assignment of a molecular force field is carried out by accessing force field parameters from the file unit 9 and then assigning these parameters to each atom or bond.

(4) Assignment Example

The following indicates a specific example of processing from the above-mentioned fragment extraction processing (S6) to the above-mentioned atom type/bond type assignment processing (S13).

Figure 4:
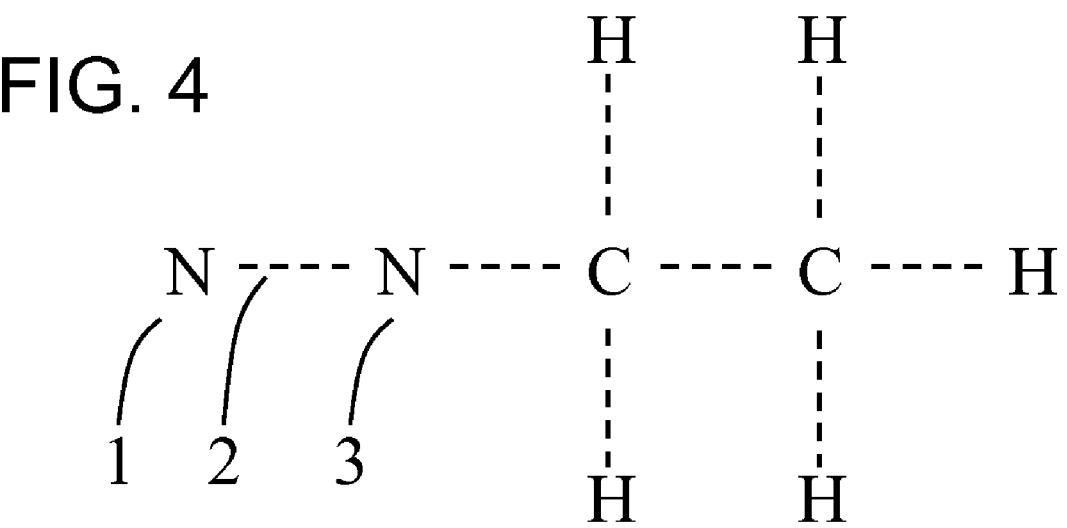
FIG. 4 is an example of a new compound for allocating molecular force field.

The input molecular structure is the same as that depicted as FIG. 4.

First, the ethylene group ($C_2H_5$—) is extracted from the molecular structure of FIG. 4 (S6).

Next, the atom type and bond type specified based on the experimental result are assigned to the atoms and bonds in the ethylene group (S7).

Since "assignment of atom type/bond type" has not yet been completed for the pair of nitrogen atoms located on the left end in FIG. 4 at this stage, a molecular force field is not able to be assigned (S8).

Next, subfragments containing pair of nitrogen atoms are accessed from the file unit 9, and an $N_2C$— subfragment that matches the molecular structure of FIG. 4 is found among those subfragments (S9).

Figure 5A:
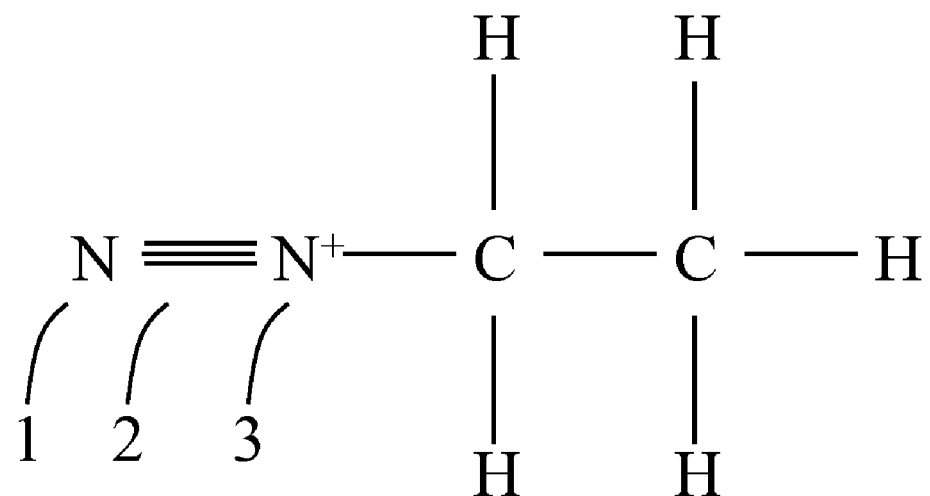
FIG. 5 is a candidate for a combination of "atom type and bond type.
Figure 5B:
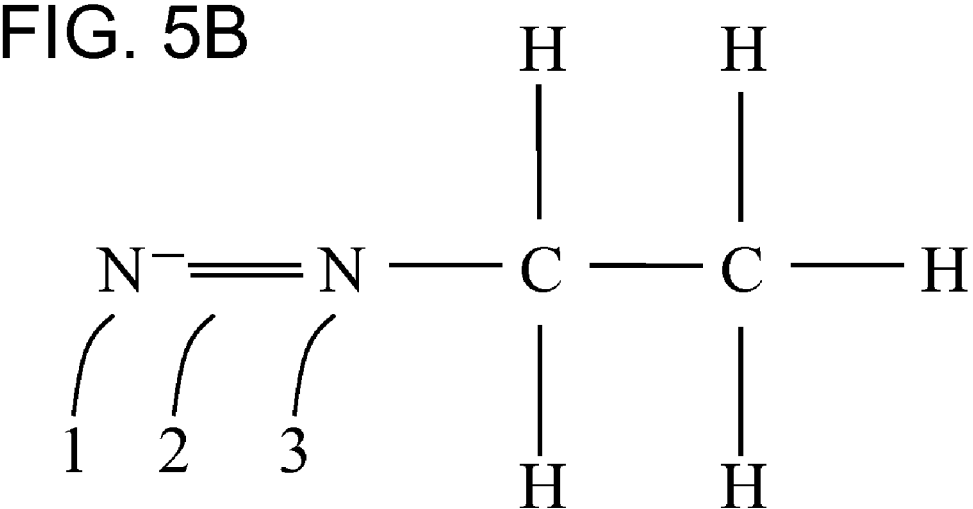
Figure 6:
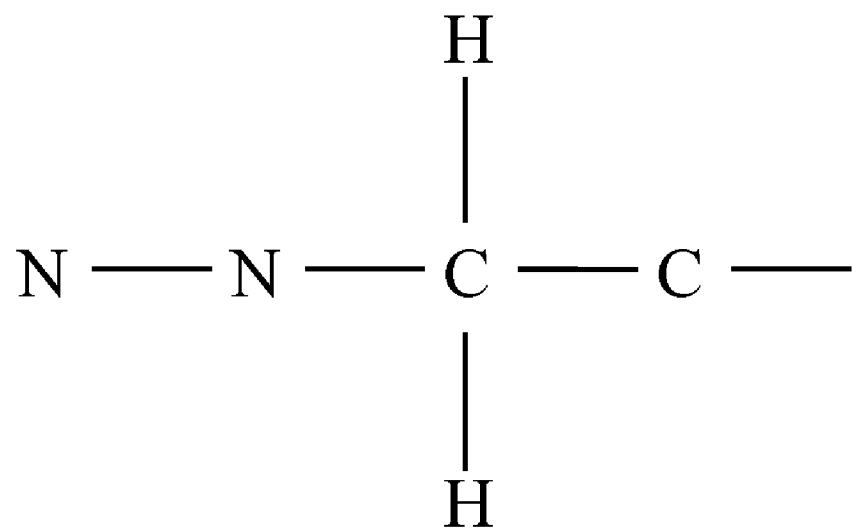
FIG. 6 is an example of fragment.

Next, candidate combinations of "atom type and bond type" depicted as FIG. 5A and FIG. 5B are specified based on the input molecular structure (S10).

Determination of candidate combinations of "atom type and bond type" is carried out based on the "Atom Type/Bond Type Classifications of Nitrogen Atoms" depicted as Table 1. The first column of Table 1 lists the charged states (cationic nitrogen, neutral nitrogen, anionic nitrogen) and the valences able to be adopted by nitrogen atoms in the $N_2C$— subfragment. The first row of Table 1 contains the coordination numbers able to be adopted by nitrogen atoms.

TABLE 1

Atom Type/Bond Type Classifications of Nitrogen Atoms

| | Univalent | Divalent | Trivalent | Tetravalent |
|---|---|---|---|---|
| Cation (quadric-valence) | Not applicable | $N\equiv N^+-$ $-N^+\equiv C-$ $=N^+=C$ 25 | $N^+=$ 23 | $N^+$ 21 |
| Neutral (tri-valence) | 25 $N\equiv C-$ 25 | $-N=C$ 24 | $N-$ 21/22/23 | Not applicable |
| Anion (di-valence) | $N=C$ 25 | $-N^--C-$ 21/22 | Not applicable | Not applicable |
| Bond Type | Double bond Triple bond | Single bond Double bond Triple bond Coordinate bond Aromatic bond | Single bond Double bond Coordinate bond Aromatic bond Delocalized bond | Single bond Coordinate bond |

The fragments depicted as Table 1 are examples of fragments including nitrogen atoms types applicable to each cell. For example, three examples of fragments containing cationic divalent nitrogens are depicted as the second row of the third column. In addition, the code for these cationic divalent nitrogens, namely 25, is also depicted as the second row of the third column. In addition, bond types able to be adopted by the atom types listed in each column are depicted as the bottom row of Table 1.

Candidate combinations of "atom type and bond type" are specified for the pairs of nitrogen atoms on the left end of FIG. 4 based on this table.

The first nitrogen atom 1 can be seen from FIG. 4 to be univalent. Thus, the atom type of this first nitrogen atom 1 can be determined from Table 1 to be either a univalent neutral nitrogen (25) or an anionic univalent nitrogen (25). Furthermore, the numbers in parentheses also indicate the above-mentioned codes used in the AMBER program. This applies similarly in the subsequent descriptions.

In addition, the second nitrogen atom 3 can be seen from FIG. 4 to be divalent. In addition, since the atom type of the first nitrogen is a univalent neutral nitrogen (valence: 3) or an anionic univalent nitrogen (valence: 2), and the valence of the ethylene group bound to the second nitrogen atom is 1, a possible valence of the second nitrogen atom 3 can be determined to be 4 or 3. The atom type of the second nitrogen atom 3 can therefore be determined to be either a cationic divalent nitrogen (25) or divalent neutral nitrogen (24) from the above information and Table 1.

Furthermore, the charged state of nitrogen atoms can be determined from the Mulliken charge obtained from the results of molecular orbital method calculations. Thus, the Mulliken charge can also be used as a basis when specifying atom type from Table 1.

On the basis of the above results, the molecular structure of FIG. 5A including a univalent neutral nitrogen (25), a triple bond and a cationic divalent nitrogen (25), and the molecular structure of FIG. 5B including an anionic univalent nitrogen (25), a double bond and a divalent neutral nitrogen (24), are derived as candidate combinations of "atom type and bond type".

Next, bond type is specified from the threshold values associated with the $N_2C-$ subfragment (0.112 nm and 0.115 nm) and the interatomic distance calculated using a molecular orbital method calculation (S11).

According to the molecular orbital method calculation, the nitrogen interatomic distance for the molecular structure of FIG. 4 is determined to be 0.11093 nm. Since this value is smaller than the threshold value of 0.112 nm which distinguishes a triple bond from an anionic/cationic double bond, the bond types of nitrogen atoms 1 and 3 can be determined to be triple bonds (03). Thus, the bond type between the nitrogen atoms is specified as a triple bond (03). Next, a "combination of atom type and bond type" is then specified based on this result and the candidate combinations depicted as FIGS. 5A and 5B (S12).

Among the candidate combinations depicted as FIGS. 5A and 5B, a molecular structure having a triple bond is depicted as FIG. 5A. Thus, the combination of a univalent neutral nitrogen (25), triple bond (03) and cationic divalent nitrogen (25) is assigned for the combination.

Finally, a molecular force field is assigned for the pair of nitrogen atoms depicted as FIG. 4 based on the combination (25-03-25) specified in the previous step (S12).

The assignment of a molecular force field to a pair of nitrogen atoms as explained above is the most difficult type of assignment. Thus, assignment of molecular force fields to other atoms can also be carried out in the same manner as the previously described embodiment.

INDUSTRIAL APPLICABILITY

The present invention can be used when simulating the properties of a novel compound in the chemical industry, and particularly in the pharmaceutical industry.

The invention claimed is:

1. A molecular force field assignment method for assigning a molecular force field to atoms constituting a molecule having a desired molecular structure and a bond connecting the atoms, the molecular force field assignment method comprising:

a first step of, in a case a single combination is unable to be specified from candidates for a combination made up of respective atom types of mutually bonded first and second atoms constituting the molecule and a bond type of a bond connecting the first and second atoms, specifying candidates for the combination that satisfy both first fragment information indicative of a type of an atom bound to the first atom, a coordination number of the first atom, and a valence able to be adopted by the first atom, and second fragment information indicative of a type of an atom bound to the second atom, a coordination number of the second atom, and a valence able to be adopted by the second atom;

a second step of specifying the combination from among the candidates specified in the first step according to whether or not an interatomic distance between the first and second atoms, obtained by analyzing the molecular structure with a molecular orbital method, exceeds a prescribed threshold value; and a third step of assigning a molecular force field to the first and second atoms and the bond connecting the first and the second atoms, based on the combination specified in the second step.

2. The molecular force field assignment method according to claim 1, wherein the prescribed threshold value is determined based on the interatomic distance obtained by analyzing a molecular structure of a molecule, having the first and second atoms for which the combination thereof has been specified, with a molecular orbital method.

3. The molecular force field assignment method according to claim 1, wherein, in a case the desired molecular structure is a structure in which the first and second atoms are nitrogen atoms, the first atom is bound only to the second atom, and the second atom is bound only to a carbon atom, the second step comprises:
specifying, as the combination, a candidate in which atom types of the first and second atoms are a neutral univalent nitrogen and a cationic divalent nitrogen, respectively, and a bond type of a bond connecting the first and second atoms is a triple bond in a case the interatomic distance between the first and second atoms as obtained by analyzing the molecular structure with a molecular orbital method is less than 0.112 nm,
specifying, as the combination, a candidate in which atom types of the first and second atoms are an anionic univalent nitrogen and a cationic divalent nitrogen, respectively, and a bond type of a bond connecting the first and second atoms is a double bond in a case the interatomic distance between the first and second atoms as obtained by analyzing the molecular structure with a molecular orbital method is more than 0.112 nm but less than 0.115 nm, and
specifying, as the combination, a candidate in which atom types of the first and second atoms are an anionic univalent nitrogen and a neutral divalent nitrogen, respectively, and a bond type of a bond connecting the first and second atoms is a double bond in a case the interatomic distance between the first and second atoms as obtained by analyzing the molecular structure with a molecular orbital method is more than 0.115 nm.

4. A molecular force field assignment apparatus for assigning a molecular force field to atoms constituting a molecule having a desired molecular structure and a bond connecting the atoms, the molecular force field assignment apparatus comprising:
a first unit which, in a case a single combination is unable to be specified from candidates for combination made up of respective atom types of mutually bonded first and second atoms constituting the molecule and a bond type of a bond connecting the first and second atoms, specifies candidates for the combination that satisfy both first fragment information indicative of a type of an atom bound to the first atom, a coordination number of the first atom, and a valence able to be adopted by the first atom, and second fragment information indicative of a type of an atom bound to the second atom, a coordination number of the second atom, and a valence able to be adopted by the second atom;
a second unit which specifies the combination from among the candidates specified by the first unit according to whether or not an interatomic distance between the first and second atoms, obtained by analyzing the molecular structure with a molecular orbital method, exceeds a prescribed threshold value; and
a third unit which assigns a molecular force field to the first and second atoms and the bond connecting the first and second atoms, based on the combination specified by the second unit.

5. The molecular force field assignment apparatus according to claim 4, wherein the prescribed threshold value is determined based on the interatomic distance obtained by analyzing a molecular structure of a molecule, having the first and second atoms for which the combination thereof has been specified, with a molecular orbital method.

6. The molecular force field assignment apparatus according to claim 4, wherein, in a case the desired molecular structure is a structure in which the first and second atoms are nitrogen atoms, the first atom is bound only to the second atom, and the second atom is bound only to a carbon atom, the second unit:
specifies, as the combination, a candidate in which atom types of the first and second atoms are a neutral univalent nitrogen and a cationic divalent nitrogen, respectively, and a bond type of a bond connecting the first and second atoms is a triple bond in a case the interatomic distance between the first and second atoms as obtained by analyzing the molecular structure with a molecular orbital method is less than 0.112 nm,
specifies, as the combination, a candidate in which atom types of the first and second atoms are an anionic univalent nitrogen and a cationic divalent nitrogen, respectively, and a bond type of a bond connecting the first and second atoms is a double bond in a case the interatomic distance between the first and second atoms as obtained by analyzing the molecular structure with a molecular orbital method is more than 0.112 nm but less than 0.115 nm, and
specifies, as the combination, a candidate in which atom types of the first and second atoms are an anionic univalent nitrogen and a neutral divalent nitrogen, respectively, and a bond type of a bond connecting the first and second atoms is a double bond in a case the interatomic distance between the first and second atoms as obtained by analyzing the molecular structure with a molecular orbital method is more than 0.115 nm.

7. A non-transitory computer readable medium containing computer instructions stored therein for causing a computer processor to perform a molecular force field assignment program for causing a computer to carry out molecular force field assignment processing for assigning a molecular force field to atoms constituting a molecule having a desired molecular structure and a bond connecting the atoms, the program causing the computer to execute:
a first step of, in a case a single combination is unable to be specified from candidates for a combinations made up of respective atom types of mutually bonded first and second atoms constituting the molecule and a bond type of a bond connecting the first and second atoms, specifying candidates for the combination that satisfy both first fragment information indicative of a type of an atom bound to the first atom, a coordination number of the first atom, and a valence able to be adopted by the first atom, and second fragment information indicative of a type of an atom bound to the second atom, a coordination number of the second atom, and the valence able to be adopted by the second atom;
a second step of specifying the combination from among the candidates specified in the first step according to whether or not an interatomic distance between the first and second atoms, obtained by analyzing the molecular structure with a molecular orbital method, exceeds a prescribed threshold value; and
a third step of assigning a molecular force field to the first and second atoms and the bond connecting the first and second atoms, based on the combination specified in the second step.

8. The non-transitory computer readable medium containing computer instructions stored therein for causing a computer processor to perform the molecular force field assignment program according to claim 7, wherein the prescribed threshold value is determined based on the interatomic distance obtained by analyzing a molecular structure of a molecule, having the first and second atoms for which the combination thereof has been specified, with a molecular orbital method.

9. The non-transitory computer readable medium containing computer instructions stored therein for causing a computer processor to perform the molecular force field assignment program according to claim 7, wherein, in a case the desired molecular structure is a structure in which the first and second atoms are nitrogen atoms, the first atom is bound only to the second atom, and the second atom is bound only to a carbon atom, the second step comprises:

specifying, as the combination, a candidate in which atom types of the first and second atoms are a neutral univalent nitrogen and a cationic divalent nitrogen, respectively, and a bond type of a bond connecting the first and second atoms is a triple bond in a case the interatomic distance between the first and second atoms as obtained by analyzing the molecular structure with a molecular orbital method is less than 0.112 nm, specifying, as the combination, a candidate in which atom types of the first and second atoms are an anionic univalent nitrogen and a cationic divalent nitrogen, respectively, and a bond type of a bond connecting the first and second atoms is a double bond in a case the interatomic distance between the first and second atoms as obtained by analyzing the molecular structure with a molecular orbital method is more than 0.112 nm but less than 0.115 nm, and specifying, as the combination, a candidate in which atom types of the first and second atoms are an anionic univalent nitrogen and a neutral divalent nitrogen, respectively, and a bond type of a bond connecting the first and second atoms is a double bond in a case the interatomic distance between the first and second atoms as obtained by analyzing the molecular structure with a molecular orbital method is more than 0.115 nm.

* * * * *